United States Patent [19]

Johnson

[11] Patent Number: 5,161,973

[45] Date of Patent: Nov. 10, 1992

[54] TUBULAR DENTAL POST

[76] Inventor: William B. Johnson, 5010 E. 68th St., Suite 104, Tulsa, Okla. 74136

[21] Appl. No.: 736,465

[22] Filed: Jul. 26, 1991

Related U.S. Application Data

[62] Division of Ser. No. 574,214, Aug. 28, 1990, Pat. No. 5,085,586.

[51] Int. Cl.$^5$ ............................................... A61C 5/08
[52] U.S. Cl. ..................................................... 433/221
[58] Field of Search ................. 433/81, 165, 220, 221, 433/224

[56] References Cited

U.S. PATENT DOCUMENTS

| 313,738 | 3/1885 | How | 433/221 |
|---|---|---|---|
| 328,837 | 10/1885 | Case | 433/221 |
| 644,803 | 3/1900 | Justi | 433/220 |
| 1,123,730 | 1/1915 | Greenfield | 433/165 |
| 1,397,067 | 11/1921 | Williams | 433/221 |
| 1,524,409 | 1/1925 | Simmons | 433/221 |
| 4,480,997 | 11/1984 | Deutsch et al. | 433/221 |
| 4,622,012 | 11/1986 | Smoler | 433/221 |
| 4,820,156 | 4/1989 | Ross | 433/165 |

FOREIGN PATENT DOCUMENTS 732124 6/1955 United Kingdom ................ 433/165

Primary Examiner—John J. Wilson
Attorney, Agent, or Firm—Head and Johnson

[57] ABSTRACT

Method of installing a post in a tooth having a metal obturator therein including the steps of drilling a borehole in the tooth with a tubular burr having a tubular opening therein of internal diameter at least slightly greater than the diameter of the obturator to thereby provide a borehole of selected internal diameter having the metal obturator remaining essentially therein, the obturator serving to assist in the guiding of the burr and inserting a tubular post into the borehole, the post receiving the metal obturator therein, the post extending partially above the top of the tooth to provide means for attachment of a crown or the like.

1 Claim, 2 Drawing Sheets

U.S. Patent  Nov. 10, 1992  Sheet 1 of 2  5,161,973
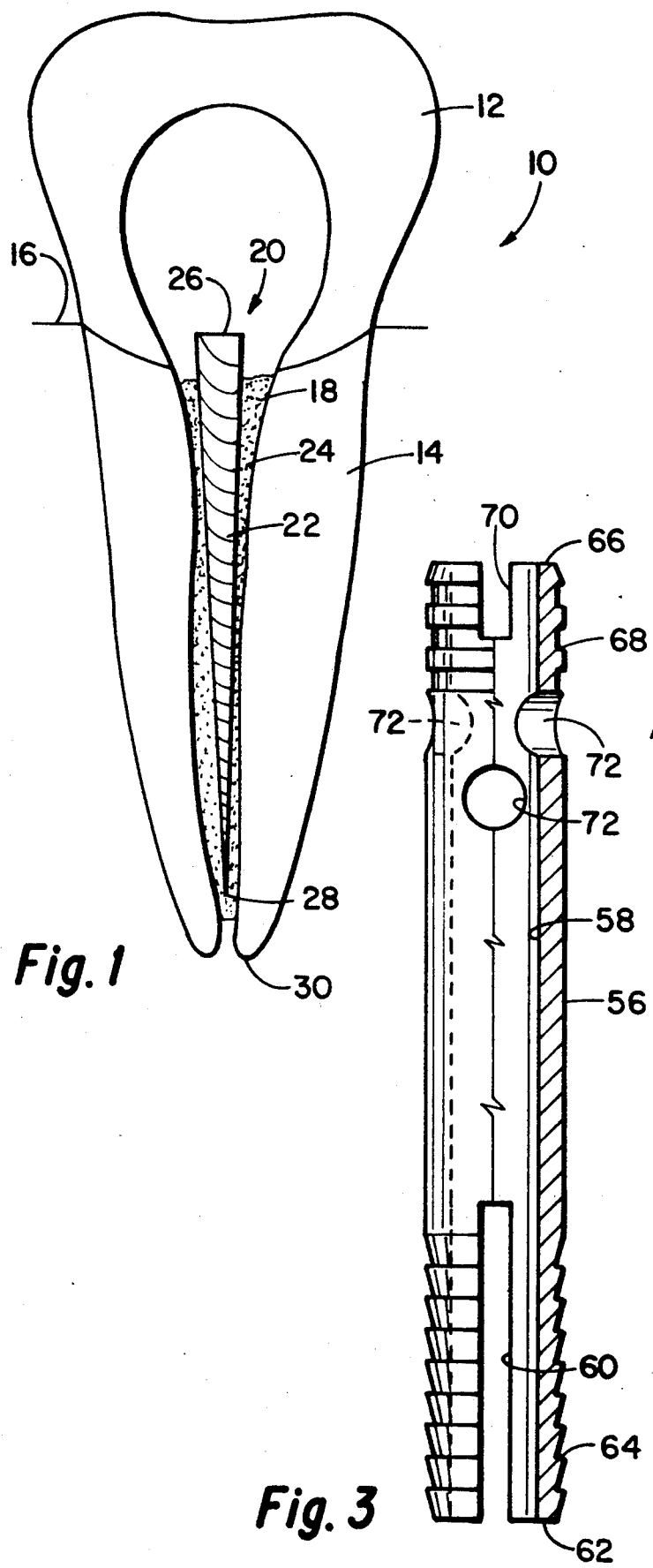
Fig. 1
Fig. 3
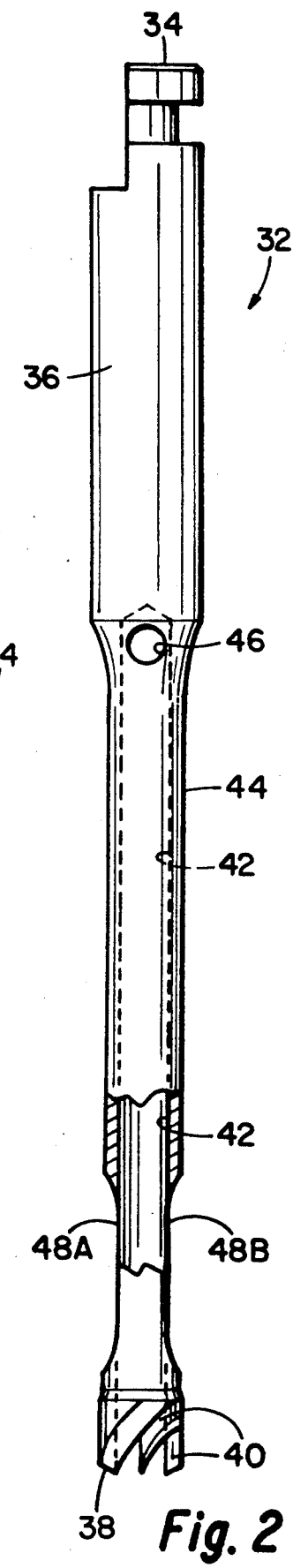
Fig. 2

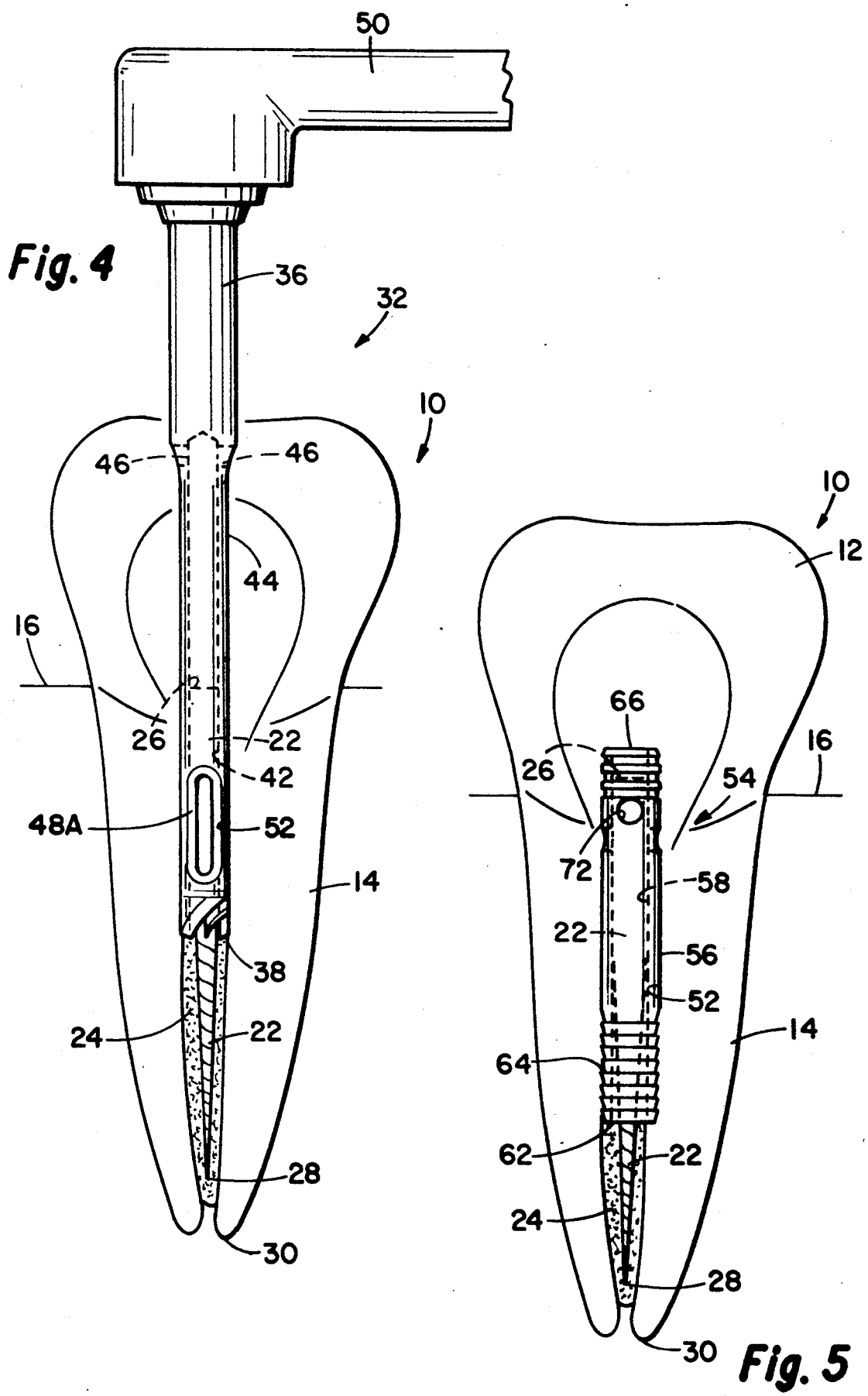

TUBULAR DENTAL POST

This is a divisional application of copending Ser. No. 07/574,214 filed on Aug. 28, 1990 now U.S. Pat. No. 5,085,586.

SUMMARY OF THE INVENTION

An elongated tubular dental burr for use in providing a borehole in a tooth with a metal obturator is provided, and a tubular dental post for insertion into a borehole having an obturator therein is described.

The installation of a metal post in a human tooth, for use in securing a crown or as a means of anchoring dental appliances has been known for many years. U.S. Pat. No. 313,738 issued to How in 1885 describes the steps of installing a post in a tooth and the use of the post for supporting a crown, thus, while the installation of posts has been known in dentistry for many years, the use of posts in dentistry in recent years has become more widespread.

The typical technique for use and installing a post in a tooth is to drill a borehole of a selected diameter and depth in the tooth. A post dimensioned to be received in the borehole is then installed and cemented into position. Typically, the post extends upwardly beyond the natural outer limit of the tooth and thus provides an anchoring point for securing a crown to the tooth and supporting the crown structurally. In other applications the portion of the post extending beyond the tooth is used for anchoring dentures, partial dentures, and so forth.

Another technique which has been more commonly employed in dentistry in recent years is that of endodontics. While endodontics has been known in dentistry for a long time, in recent years it has been more frequently and commonly applied. Whereas in the early times when the root canal of a tooth became defective and therefore painful to the patient, the common expedient was simply to remove the tooth. Now, the typical dentist removes a tooth only as a last resort, and, therefore, an infected root canal is usually first treated with endodontics and if successful, the tooth is saved to perform its natural function for many years in the patient.

An important part of endodontics is filling the root canal after the pulp has been removed and the root canal sanitized to remove infected matter. The canals have historically been filled with gutta percha, and achieving complete obturation of the root canal has been somewhat difficult. A technique which has greatly solved the problem of filling an endodontically prepared root canal is by the use of obturators which typically are formed by a shaft having prepared gutta percha therein. The most common material of construction of the obturator is metal, such as stainless steel and the like. Such endodontic obturators in the form of metal shaft with gutta percha formed thereon are described in U.S. Pat. Nos. 4,758,156 and 4,894,011. Endodontic obturators having metal shafts and gutta percha prepared for direct installation into endodontically prepared root canals are sold by Tulsa Dental Products, Inc., Tulsa, Okla. under the Trademark "THERMAFIL."

While metal based endodontic obturators have proven highly successful and are frequently employed in the dental profession, a problem is introduced when it becomes necessary, after the tooth has been endodontically treated and filled with a metal obturator, to thereafter install a dental post into the tooth. Attempting to drill a hole in the usual way in which dental posts are typically installed cannot be successfully carried out if the tooth includes a metal core obturator. The obturator tends to cause the drill, or burr as it is frequently called in dental terminology, to stray from the path of the root canal which is the path preferred for a center line of a drill hole to receive a post therein. Further, it is usually undesirable to remove an obturator from an endodontically treated tooth when installing a dental post since to do so requires a second endodontic procedure to refill the root canal if the obturator is removed.

For this reason, it is highly desirable that a means be provided for installing a dental post in a tooth having been endodontically treated and wherein the tooth includes a metal base obturator.

The method of this invention includes drilling a borehole in the tooth with a metal obturator therein utilizing a tubular burr. The tubular burr has an opening of an internal diameter of at least slightly greater than the maximum diameter of the metal obturator. The tubular burr thereby provides a borehole of selected internal and external diameter and having the metal obturator remaining therein. The drilling procedure utilizing such a tubular burr permits the metal obturator in the tooth to assist in guiding the tubular burr during the drilling operation.

Thereafter, a tubular post is inserted into the drilled borehole, the post receiving the metal obturator therein.

The method herein briefly described is preferably carried out utilizing improved tubular burrs and tubular posts as will be described hereinafter with greater detail.

For background information relating to methods and apparatus for installing posts in teeth reference may be had to the following U.S. Pat. Nos. 276,920; 965,246; 3,590,486; 3,962,787 and 4,353,698.

A better understanding of the invention will be had by reference to the following description and claims, taken in conjunction with the attached drawings.

DESCRIPTION OF THE DRAWINGS

FIG. 1 is a diagrammatic illustration of a tooth having been endodontically treated with the root canal filled by metal obturator and gutta percha and is exemplary of a tooth in which it is desired to implant a metal post for use in a subsequent dental procedure, such as for the support of a crown applied to the tooth or for attachment of a partial denture or for other reasons for which dental posts are employed.

FIG. 2 is an elevational view of an improved tubular burr as preferably employed in practicing the method of this disclosure for installation of a post in a tooth of the type illustrated in FIG. 1, that is, a tooth which has been endodontically treated and has a metal obturator therein.

FIG. 3 is an elevational partial cross-sectional view showing a type of post which is preferably used in a tooth having a metal obturator therein.

FIG. 4 shows the burr of FIG. 2 being employed in the tooth as shown in FIG. 1 and the process of forming a borehole in the tooth for receiving a post therein.

FIG. 5 shows the tooth of FIG. 1 with a dental post installed in the tooth.

DESCRIPTION OF THE PREFERRED EMBODIMENT OF THE INVENTION

Referring to the drawings and first to FIG. 1, a typical tooth is indicated by the numeral 10 and includes basically a crown portion 12 and a root portion 14, the root portion being below the gum line 16. Tooth 10, like all teeth, has a root canal 18 therein. In this illustration the root canal 18 has been subject to an endodontic treatment, that is, the nerves, blood vessels, and so forth which normally occupy an interior of a natural healthy tooth have been removed. This is typically caused when the root canal becomes, or starts to become, dead or infected or for other reasons causes pain to the individual having the tooth 10. A dentist, or more commonly an endodontic dental specialist, performs the procedure of alleviating the consequences of a deteriorated or infected root canal by removing all of the nerve and other organic tissue within the tooth, leaving the root canal 18 clean and sanitized. The root canal 18 cannot be left open since otherwise body fluids would enter and the problem which arose originally with the nerve and other naturally occurring material within the root canal would reoccur. For this reason, it is imperative that the root canal be filled, and such filling is typically accomplished with the use of gutta percha.

An improved and much more expeditious procedure for filling endodontically prepare root canals is disclosed in U.S. Pat. Nos. 4,758,156 and 4,894,011, and the procedures disclosed in such previously issued patents include the use of an endodontic obturator generally indicated by the numeral 20. The endodontic obturator typically includes a metal shaft 22 having filler material 24 thereon. The obturator is inserted in the root canal 18 with the metal shaft being cut at the desired length at the upper end 26 to remain confined within the ends of the tooth. The shaft distal end 28 is adjacent the root apex 30.

As previously stated, the prepared obturator having a metal shaft 22 and filler material 24 thereon has proven to be highly successful and in common application in the United States and other countries of the world at the present time, and this method of filling an endodontically prepared root canal has proven to be very successful.

A problem does develop however if the tooth 10 later, after the endodontic work has been completed, requires the installation of a dental post. It can be easily appreciated that it is difficult to drill a hole in a tooth having the metal shaft 22 therein with the dental drills or burrs presently employed for the installation of posts. Obviously, the metal shaft 22 could be removed and a drill hole formed to receive the typical dental post. However, such removal jeopardizes the effectiveness of the dental work previously done and would require refilling the root canal 18 in that portion beyond the distal end of the post to be installed. This procedure would then introduce the possibility of problems with the second endodontic work. For that reason, removal of the metal shaft 22 for purposes of installing a dental post is not preferred.

In the method of this invention a tubular burr generally indicated by the numeral 32 in FIG. 2 is employed. The burr has a proximal end 34 which is shaped like that of a typical dental burr and is adapted to be received in the drilling system employed by dentists. Therefore, the proximal end cylindrical portion 36 is typical of the shaft sizes employed in dental drills and burrs of the type used for formation of boreholes in teeth for the receipt of dental posts therein.

The distal end 38 of the burr 32 is provided with teeth 40 and configured so that upon rotation the burr bores into a tooth.

The burr 32 has a tubular recess 42 therein and extending from the distal end 38 for a substantial portion of the length of the burr. The internal diameter of the tubular recess 42 is at least sufficient to conveniently receive the external diameter of the metal shaft 22, as shown in FIG. 1, with which the burr is to be employed.

The external cylindrical portion 44 of the burr in the end thereof having the distal end 38 is of reduced external diameter as shown. Opposed openings 46 (only one of which is seen) are preferably formed in the burr at the upper end of the tubular recess 42. Openings 46 may be considered as one opening through the burr intersecting the tubular recess 42.

Opposed flat surfaces 48A and 48B are formed in the external cylindrical surface of the reduced diameter portion 44 adjacent to the distal end 38. These flat surfaces 48A and 48B are parallel to each other and of depth to penetrate the tubular wall of the burr so that the tubular recess 42 communicates with the exterior of the burr at the areas of the flat surfaces 48A and 48B.

Openings 46 provide for the escape of gas, specifically air, as the burr is used so that air pressure does not build up in the recess 42. The openings provided by the flat surfaces 48A and 48B provide recesses for the collection of drill material.

FIG. 4 shows the use of the burr 32 in drilling a borehole into tooth 10. A typical dental drill 50 is employed which receives the distal end portion of burr 32 and provides rotor torque to the burr. The burr is fitted over the upper or proximal end of metal shaft 22 and thereby the shaft is received within the interior recess 42 formed in the burr 32. The drilling continues, the tubular burr drills the tooth on the area thereof external of shaft 22, removing the gutta percha or filling material 24, as well as sufficient tooth structure bone external of the root to provide a borehole 52 in tooth 10 of the selected diameter of the drill and of depth as selected by the dentist.

It will be observed with reference to FIG. 4 that the shaft 22 does not interfere with the action of drilling the borehole 52, and, in fact, serves as a guide for the burr 32. In addition, it would be observed that the drilling procedure shown in FIG. 4 does not disturb shaft 22 nor displace the distal end 28.

After the borehole 52 is drilled to the desired depth, the dentist removes the burr 32 and the tooth is thereby prepared to receive a dental post therein.

The dental post of the preferred embodiment is shown in FIG. 3, the post being indicated generally by the numeral 54. The post 54 has a tubular external cylindrical surface 56 and a tubular recess 58 therein. The diameter of the recess 58 is that which is at least sufficient to receive shaft 22 of the tooth of which the post is to be used.

An elongated slot 60 is formed in the post in the area of the distal end 62. The function of slot 60 is to allow the post to slightly compresses to reduce external diameter at adjacent the distal end 62 as the post is inserted in a prepared borehole in a tooth.

The external surface of the post 54 adjacent the distal end 62 is preferably provided with grooves 64 which are circumferential and of wedge-shape to resist extraction of the post after it has been inserted into a prepared borehole in a tooth.

The upper or proximal end 66 of post 54 preferably also includes circumferential grooves 68 to provide ridges so that a crown or other appliance may be more securely supported by the post. The upper configuration can vary considerably with the intent being that which will improve the permanency of the attachment of the crown or other dental appliance to the post after it is installed in the tooth. The proximal end 66 preferably also includes a short length 70 of the nature of a screw driver slot which is used by a dentist to install the post in a borehole in a tooth. The grooves 64 at the distal end of the post may be of a thread type arrangement so that the post can be securely anchored by rotating the post into position within a borehole.

It will be understood that whether the post is inserted directly into a borehole as prepared, as shown in FIG. 4, or is rotated into position will not disturb the obturator shaft 22 in the tooth.

Openings 72 are also preferably formed in the portion of the post adjacent the proximal end 66. These openings also serve to help maintain the permanence of attachment of the crown or other appliance to the post after it is fixed in a tooth.

FIG. 5 shows the post 54 installed in the borehole 52 in tooth 10. Note that the proximal end 66 of the post typically extends above the gum line 16 and provides a means for attachment of a crown or other device. Further, it should be noted that the post does not interfere with the metal shaft 22 nor does it interfere with the endodontically prepared portion of the obturator and filler material 24 in the area below the post distal end 62, that is, the area adjacent the tooth root apex 30. As seen in FIG. 5, the post 54 has been installed in a way to serve in the same way as dental posts are typically employed and without disturbing the endodontically installed obturator in the tooth root canal.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A dental post for installation in a tooth having a borehole formed therein for use to receive a crown or other dental appliance thereon, comprising:
    an elongated tubular member of generally cylindrical external configuration having an external tubular surface and having a proximal end and a distal end, said external surface adjacent said proximal end having a plurality of circumferential grooves therein, such grooves each having an external inclined wall surface configured to permit insertion of the post in a borehole in a tooth but which resists extraction of the post from a borehole, said elongated tubular member having opposed elongted slots therein each in a plane of the member tubular axis and communicating with said distal end and dimensioned to permit the portions of said post between such slots to deflect inwardly as the post is installed in a borehole in a tooth, and including at least one lateral opening communicating said interior and exterior surfaces, such lateral opening being adjacent to and spaced from said proximal end and spaced away from said elongated slots, the tubular member thereby having an intermediate portion without an opening therethrough.

* * * * *